(12) United States Patent
Allen et al.

(10) Patent No.: US 8,974,456 B2
(45) Date of Patent: Mar. 10, 2015

(54) HYBRID MEDICAL DEVICE IMPLANT WITH MIGRATION MANAGEMENT

(75) Inventors: Drew Allen, Laguna Hills, CA (US); Seth Arnold Foerster, San Clemente, CA (US)

(73) Assignee: Dallen Medical, Inc., San Clemente, CA (US)

( * ) Notice: Subject to any disclaimer, the term of this patent is extended or adjusted under 35 U.S.C. 154(b) by 0 days.

(21) Appl. No.: 13/476,669

(22) Filed: May 21, 2012

(65) Prior Publication Data

US 2014/0018808 A1    Jan. 16, 2014

Related U.S. Application Data

(60) Provisional application No. 61/487,889, filed on May 19, 2011.

(51) Int. Cl.
*A61B 17/82* (2006.01)

(52) U.S. Cl.
USPC .......................................................... 606/74

(58) Field of Classification Search
CPC ... A61B 17/82; A61B 17/842; A61B 17/8869
USPC ................ 606/70, 71, 74, 282, 285, 324, 328
See application file for complete search history.

(56) References Cited

U.S. PATENT DOCUMENTS

| | | | |
|---|---|---|---|
| 303,360 A | 8/1884 | Brunner | |
| 3,822,445 A | 7/1974 | Feng | |
| 4,279,248 A | 7/1981 | Gabbay | |
| 4,444,181 A | 4/1984 | Wevers et al. | |
| 4,535,772 A | 8/1985 | Sheehan | |
| 4,667,675 A | 5/1987 | Davis | |
| 4,730,615 A | 3/1988 | Sutherland et al. | |
| 4,813,416 A | 3/1989 | Pollak et al. | |
| 4,938,760 A | 7/1990 | Burton et al. | |
| 4,969,892 A | 11/1990 | Burton et al. | |
| 5,330,489 A | 7/1994 | Green et al. | |
| 5,366,461 A | 11/1994 | Blasnik | |
| 5,571,105 A | 11/1996 | Gundolf | |
| 5,722,976 A | 3/1998 | Brown | |
| 5,797,915 A * | 8/1998 | Pierson et al. | 606/74 |
| 5,807,214 A | 9/1998 | Riazi | |
| 5,810,854 A | 9/1998 | Beach | |
| 5,849,012 A | 12/1998 | Abboudi | |
| 5,972,006 A | 10/1999 | Sciaino, Jr. | |
| 6,066,160 A | 5/2000 | Colvin et al. | |
| 6,051,007 A | 6/2000 | Johnson et al. | |
| 6,080,185 A | 6/2000 | Johnson et al. | |
| 6,471,715 B1 | 10/2002 | Weiss | |
| 6,540,769 B1 | 4/2003 | Miller, III | |
| 6,547,725 B1 | 4/2003 | Paolitto et al. | |

(Continued)

*Primary Examiner* — Christopher Beccia
(74) *Attorney, Agent, or Firm* — Donald E. Stout; Stout, Uxa & Buyan, LLP

(57) ABSTRACT

A dynamic tissue holding device for dynamically holding two tissue portions in contact with one another includes a resilient body having a spring and a band arranged for extending about the tissue portions to be held together. The band has a first end for attachment to a first attachment portion on the resilient body and a second end for attachment to a second attachment portion on the resilient body. Stops are disposed on portions of the resilient body for limiting both the compression and expansion of the spring. The compression of the spring is limited by engagement of two of the stops with one another and the expansion of the spring is limited by engagement of at least one of the stops with the spring.

20 Claims, 2 Drawing Sheets

(56) References Cited

U.S. PATENT DOCUMENTS

| | | |
|---|---|---|
| 6,589,246 B1 | 7/2003 | Hack et al. |
| 6,648,903 B1 | 11/2003 | Pierson, III |
| 6,969,398 B2 | 11/2005 | Stevens et al. |
| 6,997,189 B2 | 2/2006 | Biggs et al. |
| 7,108,710 B2 | 9/2006 | Anderson |
| 7,341,558 B2 | 3/2008 | de la Torre et al. |
| 7,416,556 B2 | 8/2008 | Jackson |
| 7,722,632 B2 | 5/2010 | Rothstein et al. |
| 7,867,251 B2 | 1/2011 | Colleran et al. |
| 7,867,253 B2 | 1/2011 | McMichael et al. |
| 2002/0147449 A1 | 10/2002 | Yun |
| 2003/0093117 A1 | 5/2003 | Saadat |
| 2005/0075653 A1 | 4/2005 | Saadat et al. |
| 2005/0090827 A1 | 4/2005 | Gedebou |
| 2005/0149121 A1 | 7/2005 | Crombie et al. |
| 2005/0240203 A1 | 10/2005 | Fuseri et al. |
| 2005/0251209 A1 | 11/2005 | Saadat et al. |
| 2007/0073289 A1 | 3/2007 | Kwak et al. |
| 2007/0112385 A1 | 5/2007 | Conlon |
| 2007/0213725 A1 | 9/2007 | Hack |
| 2007/0276437 A1 | 11/2007 | Call et al. |
| 2007/0293863 A1 | 12/2007 | Reimels et al. |
| 2007/0293864 A1 | 12/2007 | Reimels et al. |
| 2008/0004624 A1 | 1/2008 | Olroyd |
| 2008/0015589 A1 | 1/2008 | Hack |
| 2009/0062853 A1 | 3/2009 | McMichael et al. |
| 2010/0298828 A1* | 11/2010 | Chico Roca .................. 606/74 |
| 2012/0109199 A1* | 5/2012 | Kothari et al. ............... 606/248 |

\* cited by examiner

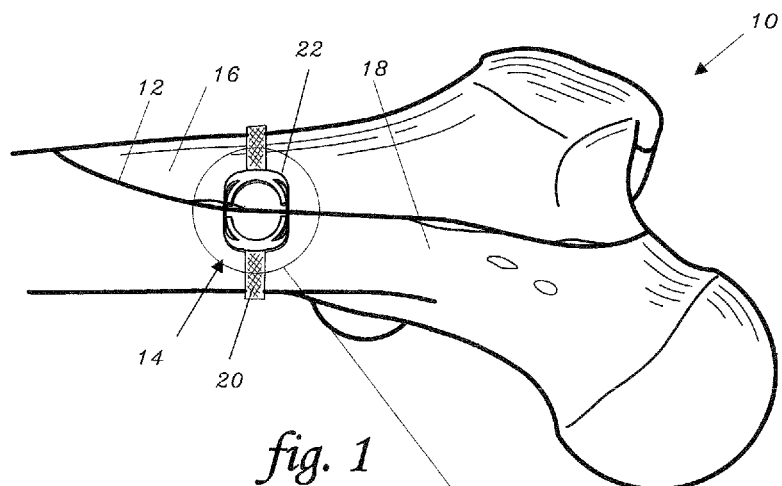
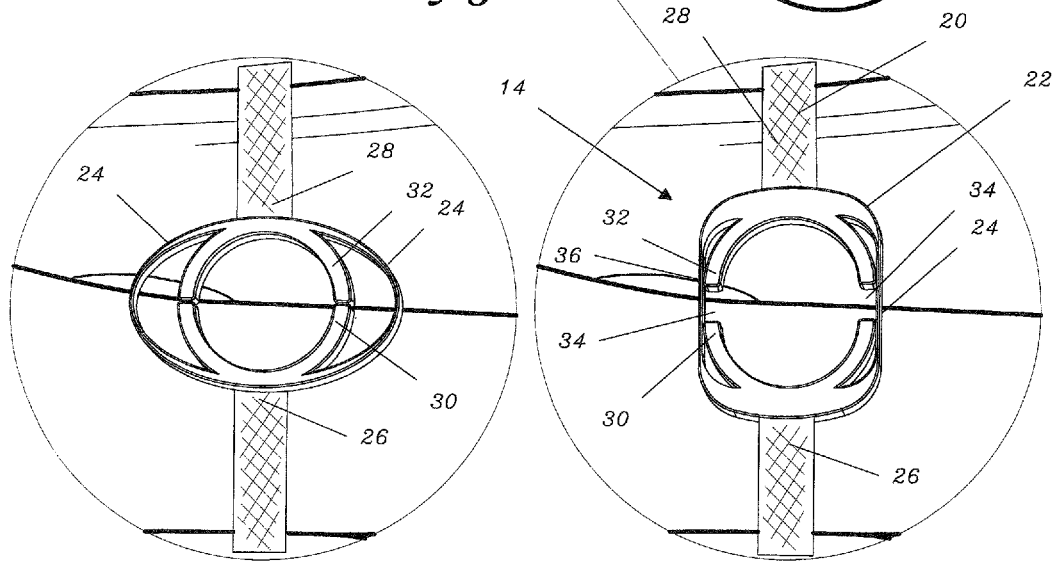
fig. 1
fig. 1a
fig. 1b

HYBRID MEDICAL DEVICE IMPLANT WITH MIGRATION MANAGEMENT

This application claims the benefit under 35 U.S.C. 119(e) of the filing date of Provisional U.S. application Ser. No. 61/487,889, entitled Hybrid Medical Device Implant with Migration Management, filed on May 19, 2011, and expressly incorporated herein by reference, in its entirety.

BACKGROUND OF THE INVENTION

The present invention is related to the general surgical repair of separated body tissues, and more particularly to internally fixating and stabilizing such body tissues, specifically bones.

In the present state of the art, there are a number of systems available to repair biological tissues separated in surgery or by injury. These products serve to approximate and stabilize the tissues so that healing may commence and provide compression in the interface to promote healing. Compression and stability are critical for proper anatomical healing of tissue. With the correct amount of compression applied to the interface of the tissue portions to be joined, signals are sent to the tissue, thus allowing the tissue to remodel in proper anatomical position. The amount of compression applied to the tissue interface needs to be appropriate to the type of tissue that is being healed.

Twisted wires are also typically used to keep bone fragments together so they may heal. Twisted wires only hold tension as long as the twisted wire pair remains stable. Often the wires untwist too soon failing to keep the bone fragments together so that they may heal. Wires can also cut into the bone fragments allowing them to separate so that healing is difficult.

When it is necessary to access the thoracic cavity for a medical procedure, for example, it is required to cut the sternum into two pieces using a rib spreader. Once the procedure is completed within the thoracic cavity, the sternum must be repaired. For such repairs, it is known to use a dynamic compression device. Some of the drawbacks of this typical device, and others which are used include:

1. Bulky spring materials, while occupying substantial space, often do not store much energy. Some use polymer elastic bands, while other use coiled springs;

2. Wires are sometimes used to wrap the bones into position in compression with one another. However, wires can have sharp ends that can damage adjunctive tissues. Knot stacks in suture can interfere with the natural movement of surrounding tissues; and 3. Current banding systems that incorporate a biasing mechanism to achieve dynamic compression put the biasing mechanism in line with the band or suture. This practice competes with precious space at the healing site. Suture or bands are used to approximate tissues so that they may heal. It is desirable to obtain the best purchase possible on the tissue, so that the binding mechanics offered by the suture may be utilized. The best purchase is optimized by ensuring that the suture has the greatest contact area with the tissue. If a biasing mechanism is interfering with this concept, the biasing mechanism may diminish the suture's ability to hold the tissues together.

In addition, the current banding systems have stiff bands that are not compliant with bony undulations. Flat sutures are used, but are tedious to tie and do not hold reliably.

The banding systems of the present invention are therefore attractive for use in sternal closure because they offer some distinct advantages over the twisted wires most commonly used in the procedure.

Bands address the issues wires have, as noted in the preceding discussion. A band, by definition, is wide. In being wide, a band distributes its forces over a wider surface area. This inhibits the band from digging into the bone. In being wide, a band affords a larger cross-sectional area whereby more material may be realized, thus presenting the opportunity to offer as much strength in the construct as is necessary to hold the bone fragments together. As such, bands address wires two main weaknesses, namely, digging into the bone fragments being held together and not having sufficient cross-sectional area.

Bands ring in other attributes other than strength and reduced pressure on the bone. Some of these attributes are difficult to manage. With strength comes stiffness, as mentioned elsewhere herein. The larger cross-section of the band significantly increases the stiffness of the band. While stiffness and rigidity are good attributes in that they can stabilize the bone union, these attributes can also prevent the band from following the contours of the bone when inserted. This can lead to capturing tissues underneath the band that ultimately destabilize the union as the tissue continue to compress and disappear over time.

Binding the band ends together can also impose some problems. Generally, this involves a mechanism on one band end that interfaces with holes or slots or contours on the other band end. This creates a tensioning system that is incremental in nature. As in the twisted wire system, this mechanical interface of the two ends is the weakest link in the system. This mechanical interface becomes stronger as the incremental steps become larger. But larger incremental steps are not conducive to fine tuning the tension, so this is problematic. Flat sutures have been used to tie tissues together, but the residual tension supplied in such a knotted structure is insufficient for optimum healing. There is a lot of fuss/time associated with trying to keep and hold a desirable tension with these flat sutures. What is needed is an attachment approach that provides variable tensioning.

Another problem associated with banding systems is that their tension holding capabilities are insufficient for the environment in which they operate. Tension holding ability can be increased or enhanced by increasing friction at the binding interface of the band. What is needed, however, is a banding system with the ability to hold tension by selectively increasing friction at the binding interface during locking and/or after locking without increasing friction while tensioning.

What is needed, therefore, are improved devices and techniques for holding two tissue portions in a state of compression and tension that address and overcome these shortcomings in an innovative way.

SUMMARY OF THE INVENTION

There is disclosed, in one aspect of the invention, a dynamic tissue holding device for dynamically holding two tissue portions in contact with one another, which comprises a resilient body and a band adapted for extending about the tissue portions to be held together. The band has a first end for attachment to a first attachment portion on the resilient body and a second end for attachment to a second attachment portion on the resilient body. The band establishes a path of tension along its length and extends linearly between the two ends of the band. The resilient body comprises a spring, a first stop having a first opposing surface, and a second stop having a second opposing surface. The resilient body may be pre-compressed to a predetermined limit of compression wherein the first and second opposing surfaces of the first and second stops, respectively, are in substantial contact with each other, such that the pre-compression of the spring applies a predetermined level of tension to the band without strangulating the tissue.

An additional stop is provided which contacts the spring when the spring is expanded a predetermined amount, so that the contact of the additional stop and the spring prevents further expansion of the spring, thereby establishing a predetermined limit of expansion of the spring. This additional stop preferably comprises a portion of one of the first and second stops, and more preferably a portion of each of the first and second stops. In one illustrated embodiment, the additional stop comprises a side surface of the first stop and a side surface of the second stop.

The spring comprises a spring portion on each of opposing sides of the resilient body, and the first and second stops each comprise generally hemispherical or horseshoe-shaped structures, in the illustrated embodiment. The first stop comprises a pair of first opposing surfaces, and the second stop comprises a pair of second opposing surfaces. A gap is disposed between the first and second opposed stop surfaces when the surfaces are not in contact, the gap being at a maximum length when the spring is expanded to the aforementioned predetermined amount. Advantageously, both the stops and the gap may be sized to establish the predetermined limits of expansion and of compression of the spring, which may comprise a leaf spring in a currently preferred embodiment.

Advantageously, the device of the invention is formed of two different materials. In one such embodiment, the resilient body comprises metal and the band bio-absorbable suture. Because of a desire to prevent the resilient body from floating within the patient's body once the suture is absorbed, in one embodiment the suture advantageously comprises a hybrid of materials, including an absorbable portion and a non-absorbable portion woven into the absorbable portion, wherein the non-absorbable suture portion will remain after absorption to provide sufficient anchoring for the resilient body to prevent migration.

In another embodiment, rather than using a hybrid suture, an eyelet is disposed on the resilient body, for receiving a fastener for attaching the resilient body to adjacent bone.

In another aspect of the invention, there is provided a dynamic tissue holding device for dynamically holding two tissue portions in contact with one another, which comprises a resilient body comprising a spring, and a band adapted for extending about the tissue portions to be held together. The band has a first end for attachment to a first attachment portion on the resilient body and a second end for attachment to a second attachment portion on the resilient body, and establishes a path of tension along its length and extending linearly between the two ends of the band. Stops are disposed on portions of the resilient body for limiting both the compression and expansion of the spring. Preferably, the compression of the spring is limited by engagement of two of the stops with one another and the expansion of the spring is limited by engagement of at least one of the stops with the spring.

Preferably, as well, the resilient body comprises metal and the band comprises bio-absorbable suture. In one embodiment, the suture comprises a hybrid of materials, including an absorbable portion and a non-absorbable portion woven into the absorbable portion. In another, alternative embodiment, the resilient body comprises an eyelet disposed on the resilient body, for receiving a fastener for attaching the resilient body to adjacent bone.

The invention, together with additional features and advantages thereof, may best be understood by reference to the following description taken in conjunction with the accompanying illustrative drawings.

BRIEF DESCRIPTION OF THE DRAWINGS

FIG. 1 illustrates a broken femur on which has been installed an implant constructed in accordance with the principles of the present invention;

FIG. 1a is a detail view of the portion of FIG. 1 denoted by the circle A, illustrating the inventive implant in its initial state;

FIG. 1b is a detail view similar to FIG. 1a, illustrating the inventive implant in its expanded state.

DESCRIPTION OF THE PREFERRED EMBODIMENT

Figure 2:
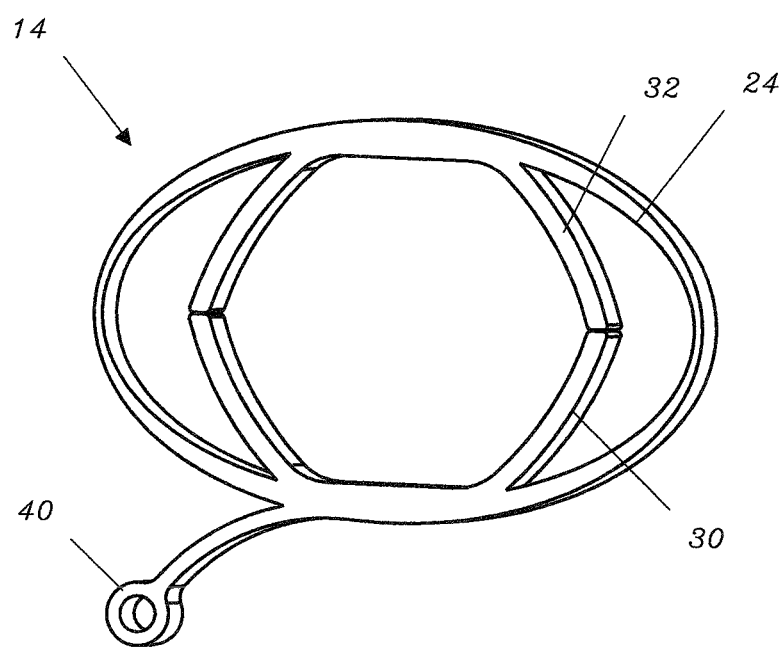
FIG. 2 is a view showing a modified embodiment of the inventive implant.

There are various groups of materials from which medical device implants should be made. Most of these materials are either absorbable or permanent. There are some situations where it is desirable to make an implant out of a hybrid of these two materials. Such a device is disclosed herein, comprising a spring tensioner and a band.

Referring now more particularly to the drawings, there is shown in FIG. 1 a broken head of a femur 10 having a fracture 12. A cerclage device 14, comprising a tension band, holds two bone fragments 16, 18, resulting from the fracture 12, together. The tension band 14 comprises suture or other suitable banding substance 20 and a resilient body 22. The tension band 14 is designed so that continuous tension is applied throughout the healing process. As bone fragments 16, 18 heal and fuse together, these fragments actually move and absorb into one another. As is desirable for optimum healing, tension band 14 supplies the forces necessary to push the bone fragments 16, 18 into one another. Optimal healing dictates that the initial forces imparted on the bone fragments 16, 18 are not as high as the physiological or native load bearing force that one would expect at the healing site. This imposes competing functions for the tensioning device 14 at its initial state. The inventive device 14 addresses the challenges presented by these competing functions by providing a mechanism that interferes with the resilient function of tensioning device 14 should excessive forces be realized.

As healing progresses, the resilient nature of the tensioning device 14 diminishes as springs 24 convert their potential energy into energy directed to pulling the suture in, as bone fragments 16, 18 move into each other. As the springs 24 lose their potential energy, the compression they are able to impart on bone fragments 16, 18 diminishes. Optimal bone healing requires that some suture tension be maintained until the end of the healing cycle. Normally a resilient mechanism decreases its rate of energy release until it approximates zero at the end of the cycle. This is not desirable according to optimal healing parameters, but is desirable to the extent that zero forces need to be realized at the end of the healing cycle in order to avoid strangulation of the tissue. Tensioning device 14 will start to act as a tourniquet and to strangle the tissue just healed. Again, there are competing functions for the tensioning device 14. The present invention addresses this problem by pre-loading the resilient mechanism with the amount of minimum energy needed to induce optimum healing.

FIG. 1a illustrates the resilient body 22 in its initial state. Spring elements 24 within the resilient body 22 serve to pull on suture ends 26, 28, which are attached to attachment portions on opposed ends of the resilient body 22 as shown, thereby tensioning the suture 20, which acts to pull the bone fragments 16 and 18 together. The spring elements 24 may be compressing the resilient body 22 such that a first opposing surface 29 (FIG. 1b) of a stop 30 is being pressed into a second opposing surface 31 (FIG. 1b) of a stop 32, on each side of the resilient body 22. This initial compression effectively preloads the resilient body 22 to ensure that tension is applied to the suture 20, which in turn compresses bone fragments 16, 18 at the end of the healing cycle. But, because stops 30, 32 come into contact with one another, via their respective opposing surfaces 29, 31, tissue strangulation is avoided. The springs 24, as illustrated, are leaf springs, and are designed to pull with the appropriate level of tension to generate optimal compression in the fracture 12, so that the femur will heal as quickly as possible.

FIG. 1b illustrates the springs 24 in their full extension, storing all of the potential energy needed to perform the functions required of the tensioning device 14. Loading springs 24 requires the tensioning of the suture ends 26, 28 into the tensioning device 14, and then locking or binding suture ends 26, 28 to the tensioning device 14 as indicated. A gap 34 is disposed between the respective opposing surfaces 29, 31 of the stops 30, 32, indicating that the resilient mechanism has been loaded with energy. Gap 34 is also the distance to be traveled during the healing process. When the gap 34 widens, each spring 24 contacts and interferes with the outwardly adjacent surfaces of its adjacent stops 30, 32, as shown in FIG. 1b. This interference between the springs and the adjacent respective stops constrains further widening of the gaps 34, by increasing, at a much higher rate, the forces necessary to further widen the gaps because of the need to overcome the interference forces. The present invention enables this higher force rate to be matched with expected physiologic or native load bearing forces. In other words, the spatial relationships between the springs 24 and the stops 30, 32 can be arranged to predetermine the maximum effective size of the gaps 34 in accordance with the desired application.

At this juncture, the tensioning device 14 is ready to provide compression between bone halves 16, 18, while also providing greater resistance to expected physiologic or native load bearing forces and while also terminating all compressive forces once the fracture 12 has fully healed.

One important feature of the invention is in the aspect of the design specification that requires the tensioning device 14 to not strangulate healing bone halves 16, 18. The two components that can supply forces that result in strangulation are the spring 24 and the suture 20. Should either of these components be made of a bio-absorbable material, that component may be designed to be absorbed before permanent strangulation is realized. In this case, the spring 24 is the likely candidate to be made out of a permanent material because of the high demands made on it (bio-absorbable materials afford inferior resiliency performance relative to a permanent material such as stainless steel).

In the disclosed embodiment, the device 14 is made of a hybrid of two materials, bio-absorbable suture 20 and a metal resilient body 22. As a result, the cerclage device 14 affords added protection against strangulation, in that its suture will absorb over time, thus limiting the ability of the device 14 to damage tissue. There is, however, another important aspect to the current invention that is realized. After the bio-absorbable suture 20 is absorbed by the body, the resilient body is free to move. This may be a serious problem, in that loose implants can migrate into joints or organs in a manner which may damage tissue. The present invention addresses this dynamic in two different embodiments.

The first embodiment, shown in FIGS. 1, 1a, and 1b, addresses the manner in which the suture absorbs. Specifically, in this embodiment, the suture 20 itself is preferably a hybrid structure. The absorbable portion, or base, of the suture 20 bears the stress or tension in the suture. A non-absorbable structure is woven into the absorbable base of the suture 20 in such a manner as to zig-zag across its profile. When the absorbable structure goes away, through absorption, the zig-zag structure expands to relieve strangulation, while still holding the resilient body in place so that it cannot migrate within the body.

FIG. 2 illustrates a second embodiment of the invention, as well as a second approach for addressing the dynamic noted above with respect to the usage of bio-absorbable suture. In other words, the embodiment of FIG. 2 shows another way of addressing the fixation of the resilient body 22 once the bio-absorbable suture 20 has absorbed. In this embodiment, the resilient body 22 includes an eyelet 40, which is configured to accept a screw. The screw passes through the eyelet 40, and into the bone, thus attaching the resilient body permanently to the bone. As thus configured, the resilient body is always fixed to the bone, and will not migrate throughout the body when the absorbable suture is absorbed by the body, thus mitigating the need to utilise the hybrid suture 20 discussed above in conjunction with the embodiment of FIG. 1.

The concepts disclosed in conjunction with this invention can be applied to many configurations of cerclage devices conceived today, and may also be applied to address bone fixation in any part of the body, not just the femur, as disclosed herein as an example only. Another suitable use, for example, would be to repair the sternum after it has been cut for the purpose of accessing the thoracic cavity. Cerclage devices may have bands or cables, instead of the sutures described herein. Cerclage devices may also have buckles or clamps, instead of the resilient body described herein. Additionally, any implant whose hybrid nature causes it to become unstable and to move around the body as the body absorbs the absorbable portion of the implant may benefit from the principles of the present invention.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention, which is to be limited only in accordance with the following claims.

What is claimed is:

1. A dynamic tissue holding device for dynamically holding two tissue portions in contact with one another, comprising:
   a resilient body; and
   a band adapted for extending about the tissue portions to be held together, the band having a first end for attachment to a first attachment portion on the resilient body and a second end for attachment to a second attachment portion on the resilient body, the band comprising a bio-absorbable material;
   the band establishing a path of tension along its length and extending linearly between the two ends of the band;
   wherein the resilient body comprises a spring, a first stop having a first opposing surface, and a second stop having a second opposing surface, wherein the resilient body may be pre-compressed to a predetermined limit of compression wherein the first and second opposing surfaces of the first and second stops, respectively, are in substantial contact with each other, such that the pre-compression of the spring applies a predetermined level of tension to the band without strangulating the tissue; and restraining structure for preventing migration of the spring locationally after the bio-absorbable material has been absorbed.

2. The device as recited in claim 1, and further comprising an additional stop which contacts the spring when the spring is expanded a predetermined amount, so that the contact of the additional stop and the spring prevents further expansion of the spring, thereby establishing a predetermined limit of expansion of the spring.

3. The device as recited in claim 2, wherein the additional stop comprises a portion of one of the first and second stops.

4. The device as recited in claim 3, wherein the additional stop comprises a portion of each of the first and second stops.

5. The device as recited in claim 4, wherein the additional stop comprises a side surface of the first stop and a side surface of the second stop.

6. The device as recited in claim 1, wherein the spring comprises a spring portion on each of opposing sides of the resilient body, and the first and second stops each comprise generally hemispherical or horseshoe-shaped structures.

7. The device as recited in claim 6, wherein the first stop comprises a pair of first opposing surfaces, and the second stop comprises a pair of second opposing surfaces.

8. The device as recited in claim 2, and further comprising a gap disposed between said first and second opposed stop surfaces when said surfaces are not in contact, the gap being at a maximum length when the spring is expanded to said predetermined amount.

9. The device as recited in claim 8, wherein the stops and the gap may be sized to establish the predetermined limits of expansion and of compression of the spring.

10. The device as recited in claim 1, wherein the restraining structure comprises non-absorbable material woven into the band along its length.

11. The device as recited in claim 1, wherein the device is comprised of two different materials.

12. The device as recited in claim 11, wherein the resilient body comprises metal.

13. The device as recited in claim 1, wherein the bio-absorbable material comprises bio-absorbable suture.

14. The device as recited in claim 10, wherein the band comprises a hybrid of materials, including the bio-absorbable material comprising one portion and the non-absorbable material comprising a non-absorbable portion woven into the absorbable portion.

15. The device as recited in claim 13, wherein the restraining structure comprises an eyelet disposed on said resilient body, for receiving a fastener for attaching the resilient body to adjacent bone.

16. A dynamic tissue holding device for dynamically holding two tissue portions in contact with one another, comprising:

a resilient body comprising a spring; and a band adapted for extending about the tissue portions to be held together, the band having a first end for attachment to a first attachment portion on the resilient body and a second end for attachment to a second attachment portion on the resilient body, the band comprising a bio-absorbable material;

the band establishing a path of tension along its length and extending linearly between the two ends of the band; and restraining structure for preventing migration of the spring locationally after the bio-absorbable material has been absorbed.

17. The device as recited in claim 16, wherein the compression of the spring is limited by engagement of two of the stops with one another and further wherein the expansion of the spring is limited by engagement of at least one of the stops with the spring.

18. The device as recited in claim 16, wherein the resilient body comprises metal and the band comprises bio-absorbable suture.

19. The device as recited in claim 16, wherein the band comprises a hybrid of materials, including the absorbable portion and a non-absorbable portion woven into the absorbable portion, the non-absorbable portion comprising said restraining structure.

20. The device as recited in claim 16, and further comprising an eyelet disposed on said resilient body, for receiving a fastener for attaching the resilient body to adjacent bone, the eyelet comprising said restraining structure.

\* \* \* \* \*